United States Patent
Hwang et al.

(10) Patent No.: US 11,884,777 B2
(45) Date of Patent: Jan. 30, 2024

(54) DIOL COMPOUND, POLYCARBONATE, AND PREPARATION METHOD OF THE SAME

(71) Applicant: LG CHEM, LTD., Seoul (KR)

(72) Inventors: Young Young Hwang, Daejeon (KR); Mooho Hong, Daejeon (KR); Ki Jae Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 407 days.

(21) Appl. No.: 17/268,271

(22) PCT Filed: Sep. 11, 2019

(86) PCT No.: PCT/KR2019/011852
§ 371 (c)(1),
(2) Date: Feb. 12, 2021

(87) PCT Pub. No.: WO2020/055178
PCT Pub. Date: Mar. 19, 2020

(65) Prior Publication Data
US 2021/0332185 A1    Oct. 28, 2021

(30) Foreign Application Priority Data
Sep. 14, 2018  (KR) .......................... 10-2018-0110537

(51) Int. Cl.
| | |
|---|---|
| C08G 64/06 | (2006.01) |
| C08G 65/48 | (2006.01) |
| C07C 43/295 | (2006.01) |
| C07D 493/04 | (2006.01) |
| C08G 64/18 | (2006.01) |
| C08G 64/28 | (2006.01) |
| C08G 65/46 | (2006.01) |

(52) U.S. Cl.
CPC .......... *C08G 65/485* (2013.01); *C07C 43/295* (2013.01); *C07D 493/04* (2013.01); *C08G 64/06* (2013.01); *C08G 64/183* (2013.01); *C08G 64/28* (2013.01); *C08G 65/46* (2013.01); *C07C 2601/16* (2017.05); *C07C 2602/10* (2017.05)

(58) Field of Classification Search
USPC ........................................................ 528/201
See application file for complete search history.

(56) References Cited

U.S. PATENT DOCUMENTS

| | | | | |
|---|---|---|---|---|
| 3,223,677 A | * | 12/1965 | Matzner | ......... C08G 64/24 528/196 |
| 3,367,978 A | | 2/1968 | White | |
| 3,843,708 A | * | 10/1974 | Matzner | ......... C08G 63/08 558/267 |
| 4,677,185 A | | 6/1987 | Heitz et al. | |
| 5,233,016 A | * | 8/1993 | Kanaka | ......... C08G 63/672 528/271 |
| 6,187,492 B1 | | 2/2001 | Ri et al. | |
| 6,262,210 B1 | | 7/2001 | Tojo et al. | |
| 6,489,386 B1 | | 12/2002 | Plotzker et al. | |
| 6,613,128 B1 | * | 9/2003 | Simonaru | ......... B29C 48/402 366/82 |
| 8,735,531 B2 | | 5/2014 | Hosokawa et al. | |
| 9,803,049 B2 | * | 10/2017 | Fernandez | ......... C08L 69/00 |
| 2003/0229256 A1 | | 12/2003 | Ishii et al. | |
| 2009/0247032 A1 | | 10/2009 | Mori et al. | |
| 2012/0226258 A1 | | 9/2012 | Otto et al. | |
| 2015/0004341 A1 | | 1/2015 | Peters | |
| 2016/0272759 A1 | | 9/2016 | Park et al. | |
| 2017/0101507 A1 | | 4/2017 | Lin et al. | |
| 2017/0298177 A1 | | 10/2017 | Lee et al. | |

FOREIGN PATENT DOCUMENTS

| | | |
|---|---|---|
| CN | 1455301 | 11/2003 |
| CN | 101654516 | 2/2010 |
| CN | 101805506 | 8/2010 |
| CN | 101805507 | 8/2010 |
| CN | 101838452 | 9/2010 |
| CN | 101845214 | 9/2010 |
| CN | 101864157 | 10/2010 |
| CN | 101935443 | 1/2011 |
| CN | 103044893 | 4/2013 |
| CN | 103059544 | 4/2013 |
| CN | 103265802 | 8/2013 |
| CN | 103275475 | 9/2013 |
| CN | 103304978 | 9/2013 |
| CN | 103351595 | 10/2013 |
| CN | 103554863 | 2/2014 |
| CN | 103724962 | 4/2014 |
| CN | 104650566 | 5/2015 |
| CN | 105017698 | 11/2015 |
| CN | 108059722 A | 5/2018 |

(Continued)

OTHER PUBLICATIONS

Office Action of Korean Patent Office in Appl'n No. 10-2018-0110537 dated Mar. 16, 2021.

(Continued)

*Primary Examiner* — Terressa Boykin

(74) *Attorney, Agent, or Firm* — Bryan Cave Leighton Paisner LLP

(57) ABSTRACT

Provided is a diol compound of the following Chemical Formula 1, a polycarbonate comprising the diol compound, and a method of producing the polycarbonate:

Chemical Formula 1

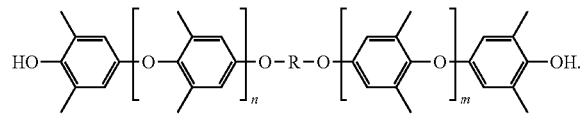

18 Claims, 8 Drawing Sheets

(56) References Cited

FOREIGN PATENT DOCUMENTS

| | | | |
|---|---|---|---|
| DE | 102009037015 | 2/2011 | |
| EP | 0144702 B1 | 6/1990 | |
| EP | 0467826 A2 | 1/1992 | |
| EP | 1642918 A1 * | 4/2006 | ........... C07C 43/295 |
| GB | 1119914 A | 7/1968 | |
| JP | S60-112823 A | 6/1985 | |
| JP | H06-157390 A | 6/1994 | |
| JP | 2010138366 A | 6/2010 | |
| JP | 2015-151513 | 8/2015 | |
| JP | 2017071775 A | 4/2017 | |
| JP | 2018509486 A | 4/2018 | |
| KR | 10-0914020 | 8/2009 | |
| KR | 10-2015-0037304 | 4/2015 | |
| KR | 10-2016-0004501 | 1/2016 | |
| KR | 10-2016-0010939 | 1/2016 | |
| KR | 10-2016-0026062 | 3/2016 | |
| KR | 10-2016-0027089 | 3/2016 | |
| KR | 10-2017-0027256 | 3/2017 | |
| KR | 10-1758962 | 7/2017 | |
| WO | 1999-14183 | 3/1999 | |
| WO | 2001-012521 | 2/2001 | |
| WO | 2010-026069 | 3/2010 | |
| WO | 2012-073970 | 6/2012 | |
| WO | 2015-002429 | 1/2015 | |

OTHER PUBLICATIONS

Office Action of Japanese Patent Office in Appl'n No. 2021-502807, dated Feb. 22, 2022.

Search Report of the European Patent Office from Appl'n No. 19860662.6, dated Jul. 7, 2021.

* cited by examiner

DIOL COMPOUND, POLYCARBONATE, AND PREPARATION METHOD OF THE SAME

CROSS-REFERENCE TO RELATED APPLICATIONS

This application is a National Stage Application of International Application No. PCT/KR2019/011852 filed on Sep. 11, 2019, which claims priority to Korean Patent Application No. 10-2018-0110537 filed on Sep. 14, 2018 with the Korean Intellectual Property Office, the disclosure of which is incorporated herein by reference in its entirety.

The present disclosure relates to a diol compound, a polycarbonate and a preparation method of the same. More specifically, it relates to a diol compound capable of preparing a polycarbonate with a novel structure having improved flame retardance, heat resistance, transparency, hardness, etc., while exhibiting excellent mechanical properties, a polycarbonate prepared using the same, and a preparation method of the polycarbonate.

BACKGROUND

Field of the Invention

A polycarbonate resin is a polymer material, which has been used in various fields such as exterior materials of electrical and electronic equipments, automobile parts, construction materials, optical components, etc., due to its physical properties such as excellent impact strength, dimensional stability, heat resistance, transparency and the like.

With a recent expansion of this polycarbonate resin into more application fields such as glass and lens, there is a demand for developing a polycarbonate with a novel structure, which has an improvement in weather resistance, refractive index and the like, while maintaining physical properties inherent in the polycarbonate resin.

Accordingly, research attempts have been made to introduce monomers with different structures into a main chain of polycarbonate by copolymerizing two or more aromatic diols with different structures, and thus obtain desired physical properties. However, most of the technologies have their limits in that the production cost is high, and an increase in chemical resistance, impact strength or the like leads to a decrease in transparency, while a rise in transparency results in a decline in chemical resistance, impact strength or the like.

Therefore, there is still a need for research and development on the polycarbonate with a novel structure having excellent flame retardance, heat resistance, transparency, hardness, and impact strength while exhibiting excellent mechanical properties such as hardness, etc., at the same time.

DETAILED DESCRIPTION

The present disclosure relates to a diol compound capable of preparing a polycarbonate having excellent flame retardance, heat resistance, hardness, and impact strength while exhibiting excellent mechanical properties, a polycarbonate prepared using the same, and a preparation method of the polycarbonate.

The present disclosure provides a diol compound of the following Chemical Formula 1.

The present disclosure also provides a polycarbonate including a diol compound of the following Chemical Formula 1, a compound of the following Chemical Formula 2, and a repeating unit derived from a carbonate precursor.

The present disclosure also provides a preparation method of a polycarbonate, including a step of polymerizing a composition containing a compound of the following Chemical Formula 1, an aromatic diol compound of the following Chemical Formula 2 and a carbonate precursor.

Hereinafter, the diol compound, the polycarbonate, and the preparation method of the same according to specific embodiments of the present invention will be described in detail.

According to one embodiment of the present disclosure, there is provided a diol compound of the following Chemical Formula 1:

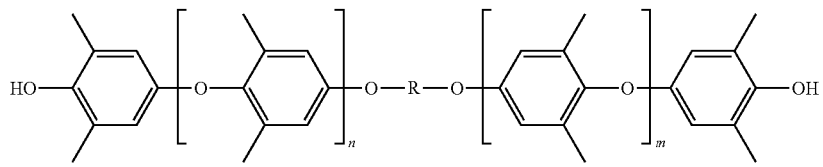

Chemical Formula 1 wherein in Chemical Formula 1:

R is a divalent group derived from benzene, biphenyl, terphenyl, or naphthalene; $C_{3-20}$ cycloalkylene unsubstituted or substituted with $C_{1-10}$ alkyl; or $C_{3-20}$ heterocycloalkylene unsubstituted or substituted with $C_{1-10}$ alkyl; and n and m are each independently an integer from 1 to 1,000.

The diol compound of Chemical Formula 1 is a polyphenylene ether-based compound, and both ends thereof are modified with a hydroxyl group to function as a diol monomer compound in polycarbonate polymerization. The compound of Chemical Formula 1 includes various arylene, cycloalkylene, or heterocycloalkylene functional groups, and thus can have an effect of improving physical properties during polycarbonate polymerization depending on characteristics of the functional group, and particularly, can impart excellent flame retardance, heat resistance, transparency, impact resistance, etc.

In the present disclosure, the alkyl group can be a linear or branched alkyl group having 1 to 10 carbon atoms, or 1 to 5 carbon atoms. As a specific example of the alkyl group, there are methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, etc., but not limited thereto.

In the present disclosure, the cycloalkylene can be a monocyclic, polycyclic, or condensed cycloalkylene group having 3 to 20 carbon atoms, or 3 to 15 carbon atoms. As a specific example of the cycloalkylene group, there are cyclopropane, cyclobutane, cyclopentane, cyclohexane, cycloheptane, cyclooctane, cyclodecane, etc., but not limited thereto.

In the present disclosure, the heterocycloalkylene means a cycloalkylene group in which at least one carbon atom constituting the cycloalkylene group is substituted with at least one hetero atom selected from the group consisting of N, O, P, Si, S and a combination thereof.

In Chemical Formula 1, specific examples of R include the following divalent groups, but the present disclosure is not limited thereto:

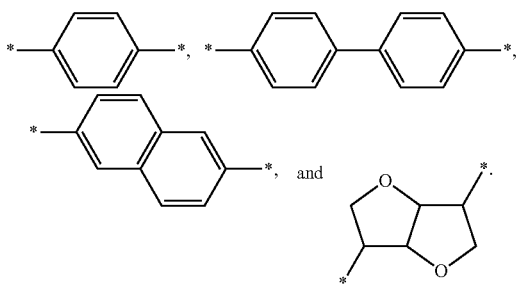

The compound of Chemical Formula 1 is a polyphenylene ether-based compound whose both ends are modified with a hydroxy group, and can be used alone or in combination with other diol compounds in polycarbonate polymerization. The polyphenylene ether can improve heat resistance and various substituent structures of R can improve hardness.

More specifically, the polycarbonate including a repeating unit derived from the diol compound of Chemical Formula 1 of the present disclosure includes a repeating unit derived from the modified polyphenylene ether structure of Chemical Formula 1 in addition to the known polycarbonate structure. Therefore, free volume of the polycarbonate chain can be reduced to improve heat resistance, and at the same time, segment rotation of the R substituent can be limited by the polyphenylene ether, thereby improving hardness of the polycarbonate.

According to one embodiment of the present disclosure, considering an effect of improving heat resistance and hardness of the polycarbonate, n and m of Chemical Formula 1 can each be an integer from 5 or more, 10 or more, or 14 or more, to 1,000 or less, 500 or less, 300 or less, or 100 or less. When n and m are too large, solubility of the compound of Chemical Formula 1 can be lowered, which may not be good for productivity or processability of the polycarbonate. On the contrary, when n and m are too small, heat resistance and/or hardness of the polycarbonate can be insufficient.

According to one embodiment of the present disclosure, a weight average molecular weight (Mw) of the compound of Chemical Formula 1 can be adjusted appropriately for its purposes and uses, and the weight average molecular weight (Mw) can be from 500 g/mol or more, 1,000 g/mol or more, or 1,500 g/mol or more, to 10,000 g/mol or less, 5,000 g/mol or less, or 3,000 g/mol or less, when measured by GPC using PS Standard.

The compound of Chemical Formula 1 can be prepared according to a known method for preparing an organic compound, and can be prepared, for example, by oxidative coupling polymerization according to the following Reaction Formula 1. The preparation method of the compound of Chemical Formula 1 will be described in more detail in the following Examples.

Reaction Formula 1

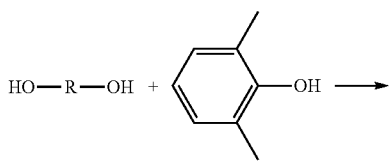

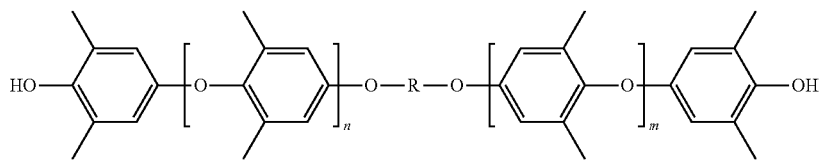

wherein in the above Reaction Formula 1, R, n and m are as defined in Chemical Formula 1.

According to another embodiment of the present disclosure, there is provided a polycarbonate including a diol compound of the following Chemical Formula 1, a compound of the following Chemical Formula 2, and a repeating unit derived from a carbonate precursor:

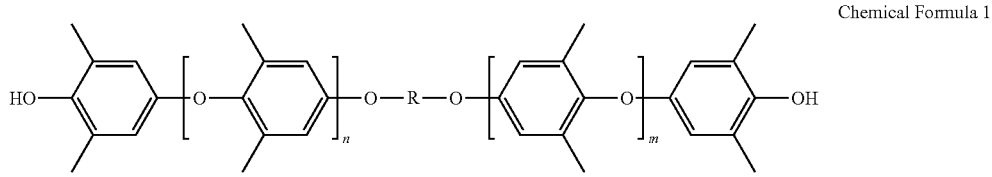

Chemical Formula 1 wherein in Chemical Formula 1:

R is a divalent group derived from benzene, biphenyl, terphenyl, or naphthalene; $C_{3-20}$ cycloalkylene unsubstituted or substituted with $C_{1-10}$ alkyl; or $C_{3-20}$ heterocycloalkylene unsubstituted or substituted with $C_{1-10}$ alkyl; and n and m are each independently an integer from 1 to 1,000,

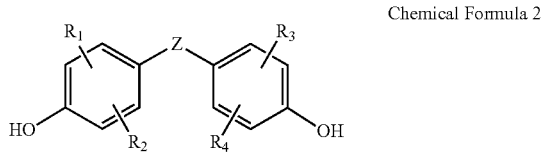

Chemical Formula 2 wherein in Chemical Formula 2:

$R_1$ to $R_4$ are each independently hydrogen, $C_{1-10}$ alkyl, $C_{1-10}$ alkoxy, or halogen; and Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

Description of Chemical Formula 1 and specific examples thereof are as described above.

The polycarbonate of the present disclosure can include only the repeating units derived from the compounds of Chemical Formulae 1 and 2. Alternatively, the polycarbonate can further include a repeating unit derived from another aromatic diol compound.

In Chemical Formula 2, $R_1$ to $R_4$ can be each independently hydrogen, or $C_{1-4}$ alkyl. Preferably, $R_1$ to $R_4$ can be each independently hydrogen, methyl, chloro, or bromo.

Also, in Chemical Formula 2, Z is linear or branched $C_{1-10}$ alkylene unsubstituted or substituted with phenyl, and more preferably can be methylene, ethane-1,1-diyl, propane-2,2-diyl, butane-2,2-diyl, 1-phenylethane-1,1-diyl, or diphenylmethylene.

The polycarbonate according to one embodiment of the present disclosure can include a repeating unit of the following Chemical Formula 3:

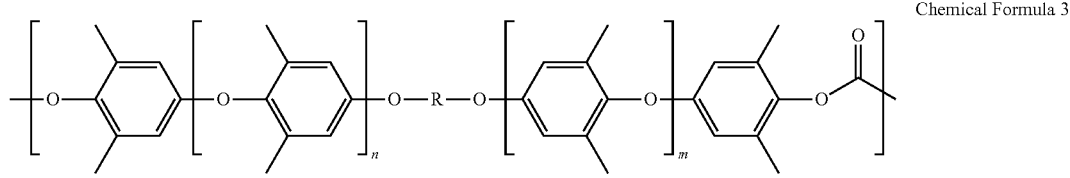

Chemical Formula 3 wherein in Chemical Formula 3:

R, n, and m are as defined in Chemical Formula 1.

In addition, the polycarbonate according to one embodiment of the present disclosure can include a repeating unit of the following Chemical Formula 4:

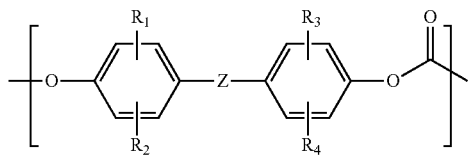

Chemical Formula 4 wherein in Chemical Formula 4:

$R_1$ to $R_4$, and Z are as defined as in Chemical Formula 1.

The repeating unit of Chemical Formula 1 is characterized by excellent heat resistance, hardness, and flame retardance, and the repeating unit of Chemical Formula 2 is characterized by excellent transparency. By controlling a molar ratio of the repeating units of Chemical Formulae 1 and 2, a polycarbonate with desired physical properties can be prepared.

When the polycarbonate of the present disclosure further includes the repeating unit of Chemical Formula 2 in addition to the repeating unit of Chemical Formula 1, the molar ratio thereof is not particularly limited. For example, the molar ratio of the repeating unit of Chemical Formula 1 and the repeating unit of Chemical Formula 2 can be 99:1 to 1:99. In a specific embodiment, the molar ratio of the repeating unit of Chemical Formula 1 and the repeating unit of Chemical Formula 2 can be 50:50 to 3:97, 30:70 to 5:95, or 15:85 to 10:90. When the molar ratio of Chemical Formula 1 is excessively low, heat resistance, hardness and flame retardance of the polycarbonate may not be sufficient. On the contrary, when the molar ratio of Chemical Formula 1 is excessively high, transparency or impact strength of the polycarbonate can be lowered or reactivity can be reduced, thereby reducing productivity of the polycarbonate.

A weight average molecular weight (Mw) of the polycarbonate can be adjusted appropriately for its purposes and uses, and the weight average molecular weight (Mw) can be from 15,000 g/mol or more, 20,000 g/mol or more, or 28,000 g/mol or more, to 50,000 g/mol or less, 40,000 g/mol or less, or 33,000 g/mol or less, when measured by GPC using PS Standard. When the weight average molecular weight (Mw) is too low, mechanical properties of the polycarbonate may not be sufficient, and when the weight average molecular weight (Mw) is too high, productivity of the polycarbonate can be lowered.

Also, a melt index of the polycarbonate, which is measured in accordance with ASTM D1238 (300° C., 1.2 kg condition), can be adjusted appropriately for its purposes and uses, and can be from 1 g/10 min or more, 3 g/10 min or more, or 8 g/10 min or more, to 100 g/10 min or less, 30 g/10 min or less, or 15 g/10 min or less.

Also, the polycarbonate can have an Izod impact strength at room temperature from 100 J/m or more, 130 J/m or more, 140 J/m or more, 145 J/m or more, or 150 J/m or more, to 1,000 J/m or less, 500 J/m or less, 300 J/m or less, 250 J/m or less, or 200 J/m or less, when measured at 23° C. in accordance with ASTM D256 (⅛ inch, Notched Izod).

Also, the polycarbonate can have a glass transition temperature (Tg) from 153° C. or more, 154° C. or more, or 155° C. or more, to 190° C. or less, 180° C. or less, 170° C. or less, 168° C. or less, or 165° C. or less, which means high heat resistance.

Also, the polycarbonate can have pencil hardness of B or HB, when measured at a 45 degree angle with a load of 50 g in accordance with ASTM D3363.

Meanwhile, according to another embodiment of the present disclosure, there can be provided a preparation method of the polycarbonate, including a step of polymerizing a composition containing a compound of the following Chemical Formula 1, an aromatic diol compound of the following Chemical Formula 2 and a carbonate precursor:

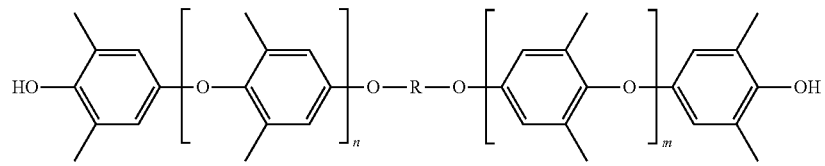

Chemical Formula 1 wherein in Chemical Formula 1:

R is a divalent group derived from benzene, biphenyl, terphenyl, or naphthalene; $C_{3-20}$ cycloalkylene unsubstituted or substituted with $C_{1-10}$ alkyl; or $C_{3-20}$ heterocycloalkylene unsubstituted or substituted with $C_{1-10}$ alkyl; and n and m are each independently an integer from 1 to 1,000,

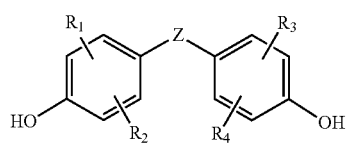

Chemical Formula 2 wherein in Chemical Formula 2:

$R_1$ to $R_4$ are each independently hydrogen, $C_{1-10}$ alkyl, $C_{1-10}$ alkoxy, or halogen; and Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

In Chemical Formula 1, specific examples of R include the following divalent groups, but the present disclosure is not limited thereto:

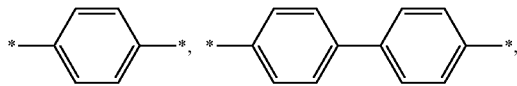

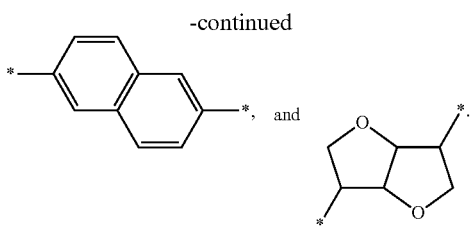

Description of the Chemical Formula 1 and specific examples thereof are as described above.

Specific examples of the aromatic diol compound of Chemical Formula 2 can include at least one compound selected from the group consisting of bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl)sulfide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane (bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, and 1,1-bis(4-hydroxyphenyl)-1-phenylethane.

Also, the carbonate precursor serves to link the compound of Chemical Formula 1 and the compound of Chemical Formula 2 to each other. A specific example of the carbonate precursor can be phosgene, triphosgene, diphosgene, bromophosgene, dimethyl carbonate, diethyl carbonate, dibutyl carbonate, dicyclohexyl carbonate, diphenyl carbonate, ditolyl carbonate, bis(chlorophenyl) carbonate, m-cresyl carbonate, dinaphthylcarbonate, bis(diphenyl) carbonate or bishaloformate.

As a method of polymerizing polycarbonate using a composition containing an aromatic diol compound of Chemical Formula 2 and a carbonate precursor in addition to the compound of Chemical Formula 1, according to one embodiment, a polymerization process can be performed on a composition containing the three precursor compounds at once.

Herein, the compound of Chemical Formula 1 can be used in an amount from 1 wt % or more, 2 wt % or more, or 3 wt % or more, to 15 wt % or less, 12 wt % or less, or 10 wt % or less based on 100 wt % of the composition.

Also, the compound of Chemical Formula 2 can be used in an amount of 40 wt % or more, 50 wt % or more, or 55 wt % or more, to 80 wt % or less, 75 wt % or less, or 70 wt % or less based on 100 wt % of the composition.

Also, the carbonate precursor can be used in an amount of 10 wt % or more, 15 wt % or more, or 20 wt % or more, to 50 wt % or less, 40 wt % or less, or 35 wt % or less based on 100 wt % of the composition.

At this time, the polymerization can be carried out by any method of an interfacial polymerization method or a melt polymerization method.

It is preferable that the interfacial polymerization is carried out at a temperature of 0° C. to 40° C. for 10 minutes to 5 hours. Also, it is preferable that a pH is maintained at 9 or more, or 11 or more during the reaction.

Any solvent can be used in the polymerization without particular limitation, as long as such solvent is used in the polymerization of the polycarbonate in the art. As an example, halogenated hydrocarbons such as methylene chloride, chlorobenzene, etc., can be used.

Also, it is preferable that the polymerization is performed in the presence of an acid binder. As the acid binder, any of the following can be used: alkali metal hydroxides such as sodium hydroxide, potassium hydroxide, etc., or amine compounds such as pyridine, etc.

Moreover, it is preferable that polymerization is carried in the presence of a molecular weight modifier, in order to control a molecular weight of the polycarbonate during the polymerization. As the molecular weight modifier, $C_{1-20}$ alkylphenol can be used. As a specific example thereof, there can be p-tert-butylphenol, p-cumylphenol, decylphenol, dodecylphenol, tetradecylphenol, hexadecylphenol, octadecylphenol, eicosylphenol, docosylphenol or triacontylphenol. The molecular weight modifier can be added thereinto before, during or after initiation of the polymerization. The molecular weight modifier can be used in an amount from 0.01 to 10 parts by weight, preferably 0.1 to 6 parts by weight per 100 parts by weight of the aromatic diol compound, and a desired molecular weight can be obtained within that range.

Also, a reaction accelerator such as a tertiary amine compound, quaternary ammonium compound, quaternary phosphonium compound, etc., for example, triethylamine, tetra-n-butylammonium bromide, tetra-n-butylphosphonium bromide, etc., can be further used in order to speed up the polymerization reactions.

Preferably, the polymerization can be carried out by a melt polymerization method.

In the interfacial polymerization, the polymerization is carried out while dissolving polymers in a solvent, so that additional efforts and time are required for purification, neutralization, etc. of the polymer. However, the melt polymerization is a polymerization method by a transesterification reaction, and can prepare polycarbonates at lower cost than the interfacial polymerization. In addition, as the interfacial polymerization is environmentally friendly by not using toxic materials such as phosgene or methylene chloride, this method has attracted attention in recent years.

The preparation method of a polycarbonate by the melt polymerization can be carried out by reacting a diol compound and a carbonic acid diester under a high-temperature and reduced-pressure condition in the presence of a catalyst to proceed the transesterification reaction. As the catalyst, a catalyst known in a metal compound catalyst system and a non-metal compound catalyst system can be used.

Specific examples of the carbonic acid diester that can be used as a starting material of transesterification can include carbonates of diaryl compounds, carbonates of dialkyl compounds, and carbonates of alkylaryl compounds, but the present disclosure is not limited thereto.

The diol compound and the carbonic acid diester can be included such that a molar ratio of the carbonic acid diester/the diol compound is 0.9 to 1.5, preferably 0.95 to 1.20, more preferably 0.98 to 1.20.

In the preparation of a polycarbonate resin through the transesterification of the present disclosure, additives such as a terminating agent, a branching agent and an antioxidant can be additionally used in the present disclosure.

The terminating agent, the branching agent, and the antioxidant can be added in the form of powders, liquids, gases, etc., and these additives improve quality of the polycarbonate resin to be obtained.

A reaction pressure of the transesterification is not particularly limited, and can be adjusted depending on a vapor pressure of the monomers used and a reaction temperature. Generally, the pressure is adjusted to a pressurized state of 1 to 10 atm (atmospheric pressure) initially, and to a reduced state of 0.1 to 100 mbar at the end of the reaction.

The transesterification can be carried out until a desired molecular weight is obtained. Generally, the transesterification is carried out for 0.2 to 10 hours.

The transesterification is usually carried out in the absence of an inert solvent, but can also be carried out in the presence of 1 to 150 wt % of an inert solvent based on the polycarbonate resin obtained, if necessary. As the inert solvent, aromatic compound such as diphenyl ether, halogenated diphenyl ether, benzophenone, polyphenylene ether, dichlorobenzene and methylnaphthalene; cycloalkane such as tricyclo(5,2,10)decane, cyclooctane and cyclodecane, etc. can be used.

In addition, the transesterification can be carried out in an inert gas atmosphere. As the inert gas, argon, carbon dioxide, nitrogen monoxide, nitrogen, chlorofluoro hydrocarbon, alkane such as ethane and propane, alkene such as ethylene and propylene, etc. can be used.

As the transesterification proceeds under the above condition, phenols, alcohols or esters thereof corresponding to the carbonic acid diester used, and the inert solvent are eliminated from the reactor. These substances can be separated, purified, and regenerated. The transesterification can be operated as batchwise process or continuous process using any device.

Any reactor equipped with a general stirrer can be used for the transesterification. A reactor capable of stirring at high viscosity is preferable, because the viscosity increases as the reaction progresses.

Preferably, the reactor is a container or an extruder.

The pre-polymerization is preferably carried out at a reaction pressure of 0.1 mbar to 100 mbar, more preferably at 1 mbar to 10 mbar. When the reaction pressure is between 0.1 to 100 mbar, the carbonic acid diester which is the starting material is not removed by distillation, and thus the composition of the transesterification system does not change. In addition, the monohydroxy compound, by-product, is removed by distillation, so that the reaction proceeds smoothly.

According to another embodiment of the present disclosure, there can be provided a molded article prepared using the polycarbonate. As described above, the polycarbonate including the repeating unit of Chemical Formula 1 has also an improvement in flame retardance, heat resistance, and transparency while having excellent mechanical properties, and thus has wider application fields compared to molded articles including existing polycarbonates. Also, a polycarbonate with desired physical properties can be prepared by adjusting the molar ratio of repeating units of Chemical Formulae 1 and 2.

In addition to the polycarbonate according to the present disclosure, the molded article can contain at least one additive selected from the group consisting of antioxidants, plasticizers, antistatic agents, nucleating agents, flame retardants, lubricants, impact modifiers, fluorescence brightening agents, ultraviolet ray absorbents, pigments and dyes, if necessary.

As one example of a preparation method of the molded article, there can be included a step of well mixing the polycarbonate according to the present disclosure and other additives with a mixer, then performing extrusion molding with an extruding machine to manufacture pellets, then drying the pellets, and then performing injection with an injection molding machine.

The present disclosure can provide a polycarbonate with a novel structure having improved flame retardance, heat resistance, impact strength, and hardness while exhibiting excellent mechanical properties, and a preparation method of the same.

DETAILED DESCRIPTION OF THE EMBODIMENTS

The present disclosure will be described in more detail through the following embodiments. However, the following embodiments are provided only for the purpose of illustrating the present disclosure, and thus the present disclosure is not limited thereto.

EXAMPLES

Example 1

(1) Preparation of monomer 4,4'-(((1,4-phenylenebis(oxy))bis(2,6-dimethyl-4,1-phenylene))bis(oxy))bis(2,6-dimethylphenol)

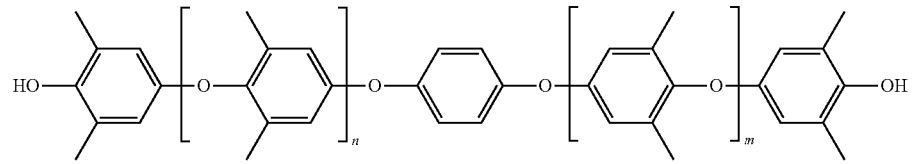

In a 1.5 L round bottom flask, 300 ml of toluene (solvent) and 40 ml of pyridine were added to 0.6 g of copper bromide (CuBr), followed by stirring at room temperature for about 5 hours while injecting oxygen. Then, 40.1 g of 2,6-dimethylphenol and 2.6 g of hydroquinone were added to 40 ml

Example 2

(1) Preparation of monomer 4,4'-((([1,1'-biphenyl]-4,4'-diylbis(oxy))bis(2,6-dimethyl-4,1-phenylene))bis(oxy))bis(2,6-dimethylphenol)

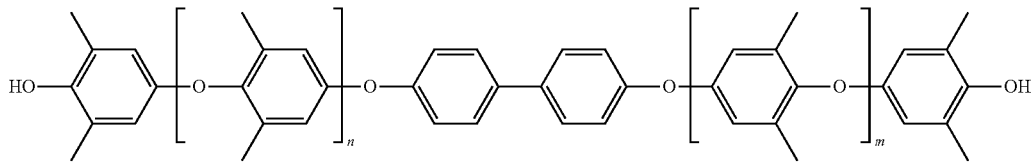

of toluene in the flask, followed by an overnight reaction at about 30° C. while injecting oxygen. Then, the reactants were placed in a separation funnel, and 200 ml of toluene and 200 ml of water were further added to separate organic layer reactants. The obtained organic substance was added to a mixed solvent of 1500 ml of methanol and 5 ml of a 35% HCl solution to precipitate the reactants. The precipitated reactants were placed in a 110° C. vacuum drying oven to completely remove the solvent to obtain a compound with the above structure in the form of about 34.2 g of white powder (Mw=2,000 g/mol, n,m=14~18).

Figure 1:
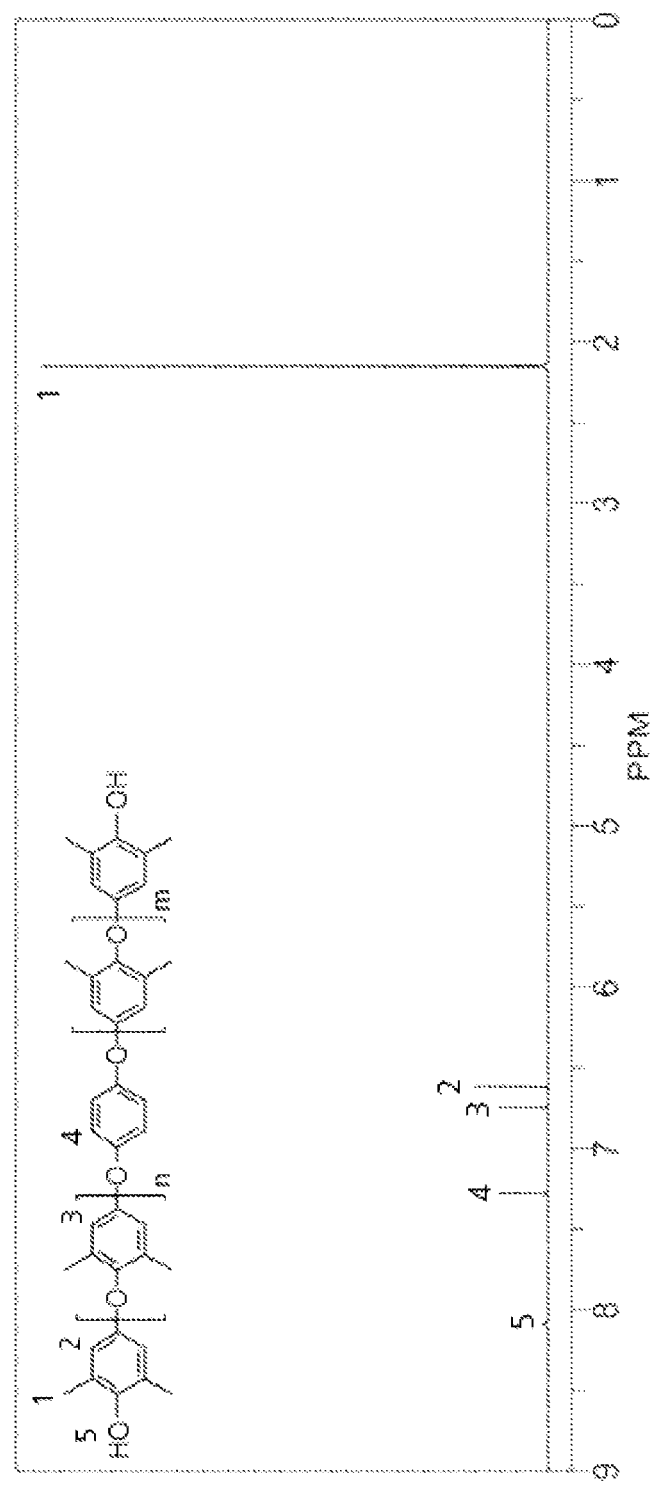
FIG. 1 is a $^1$H-NMR graph of the compound prepared in Example 1.

$^1$H-NMR of the compound is shown in FIG. 1.

(2) Preparation of Copolycarbonate 1784 g of water, 385 g of NaOH, and 233 g of BPA (bisphenol A) were added to a 2 L polymerization reactor which is equipped with a nitrogen purge and a condenser and might be kept at room temperature with a circulator, and then mixed and dissolved in a nitrogen atmosphere. 4.3 g of PTBP (para-tert butylphenol) and 26.3 g of 4,4'-(((1,4-phenylenebis(oxy))bis(2,6-dimethyl-4,1-phenylene))bis(oxy))bis(2,6-dimethylphenol) prepared in step (1) were separately dissolved in MC (methylene chloride) and added to the polymerization reactor. Then, 130 g of TPG (triphosgene) was dissolved in MC, and the solution was slowly added thereto for 1 hour while maintaining the pH at 11 or more with 20% aqueous NaOH solution. After 10 minutes, 46 g of TEA (triethylamine) was added to carry out a coupling reaction. After 1 hour and 20 minutes in total, TEA was removed by lowering the pH to 4 or less with 35% HCl solution, and washed 3 times with distilled water to adjust the pH of the produced polymer to 6 to 7 (neutral). The polymer thus produced was obtained by reprecipitation in a mixed solution of methanol and hexane, and then dried at 120° C. to prepare a final copolycarbonate (molar ratio of Chemical Formula 1: Chemical Formula 2=about 10: 90).

Figure 2:
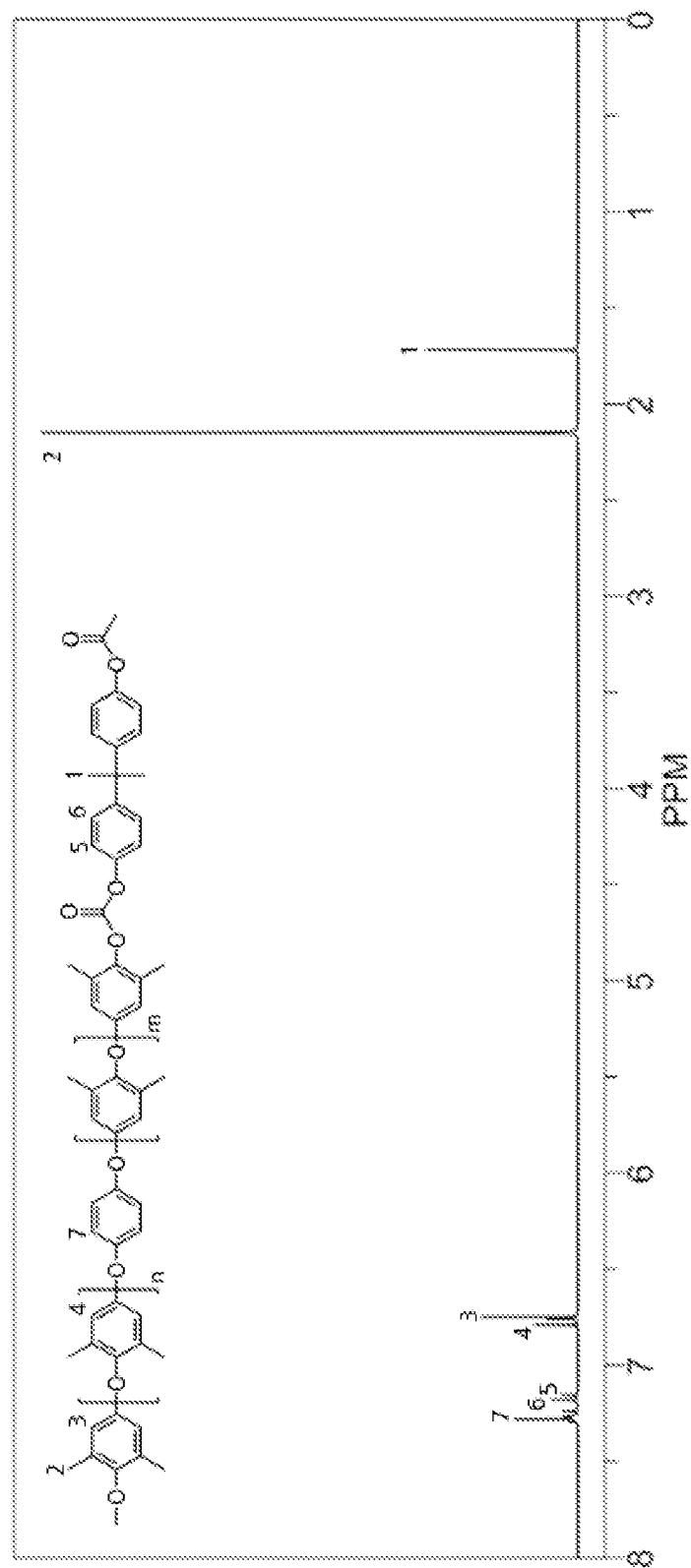
FIG. 2 is a $^1$H-NMR graph of the copolycarbonate prepared in Example 1.

$^1$H-NMR of the copolycarbonate thus prepared is shown in FIG. 2.

A compound with the above structure was prepared in the form of about 32.1 g of yellow powder in the same manner as in Example 1, except that 4.5 g of (1,1'-biphenyl)-4,4'-diol was used instead of 1.3 g of hydroquinone in the above (1) Preparation of monomer of Example 1 (Mw=2,200 g/mol, n,m=12~18).

Figure 3:
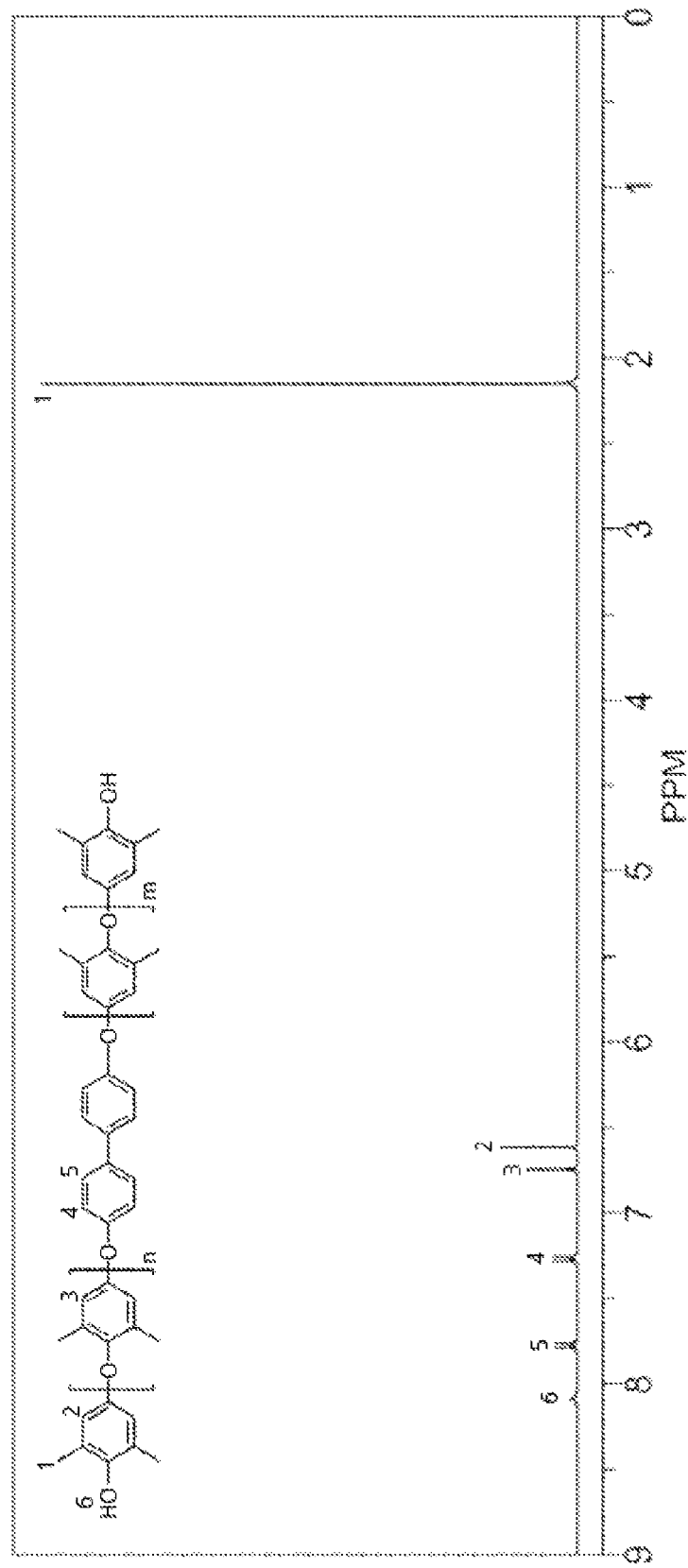
FIG. 3 is a $^1$H-NMR graph of the compound prepared in Example 2.

$^1$H-NMR of the compound is shown in FIG. 3.

(2) Preparation of Copolycarbonate

A copolycarbonate resin was prepared in the same manner as in Example 1, except that 26.3 g of 4,4'-((([1,1'-biphenyl]-4,4'-diylbis(oxy))bis(2,6-dimethyl-4,1-phenylene))bis(oxy))bis(2,6-dimethylphenol) was used instead of 26.3 g of 4,4'-(((1,4-phenylenebis(oxy))bis(2,6-dimethyl-4,1-phenylene))bis(oxy))bis(2,6-dimethylphenol) in the above (2) Preparation of copolycarbonate of Example 1 (molar ratio of Chemical Formula 1: Chemical Formula 2=about 10:90).

Figure 4:
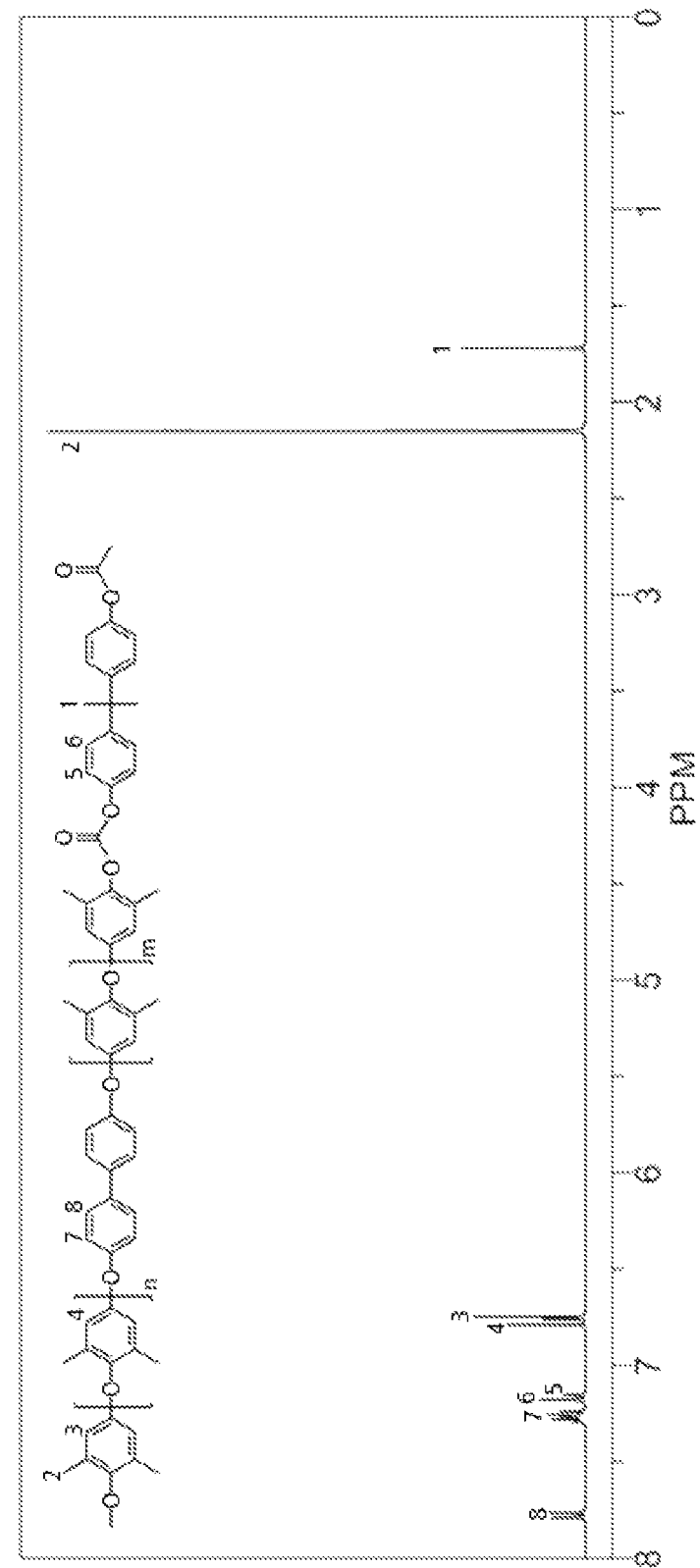
FIG. 4 is a $^1$H-NMR graph of the copolycarbonate prepared in Example 2.

$^1$H-NMR of the copolycarbonate thus prepared is shown in FIG. 4.

Example 3

(1) Preparation of monomer 4,4'-(((naphthalene-2,6-diylbis(oxy))bis(2,6-dimethyl-4,1-phenylene))bis(oxy))bis(2,6-dimethylphenol)

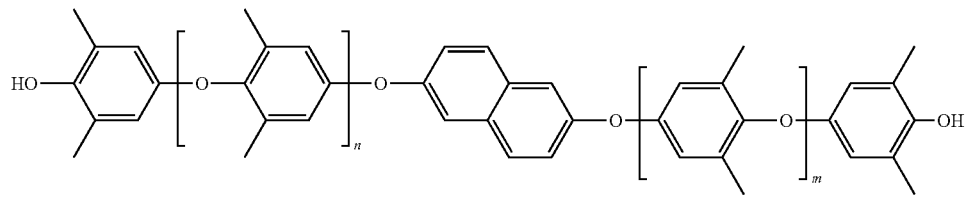

A compound with the above structure was prepared in the form of about 32.9 g of yellow powder in the same manner as in Example 1, except that 1.9 g of naphthalene-2,6-diol was used instead of 1.3 g of hydroquinone in the above (1) Preparation of monomer of Example 1 (Mw=2,100 g/mol, n,m=14~18).

Figure 5:
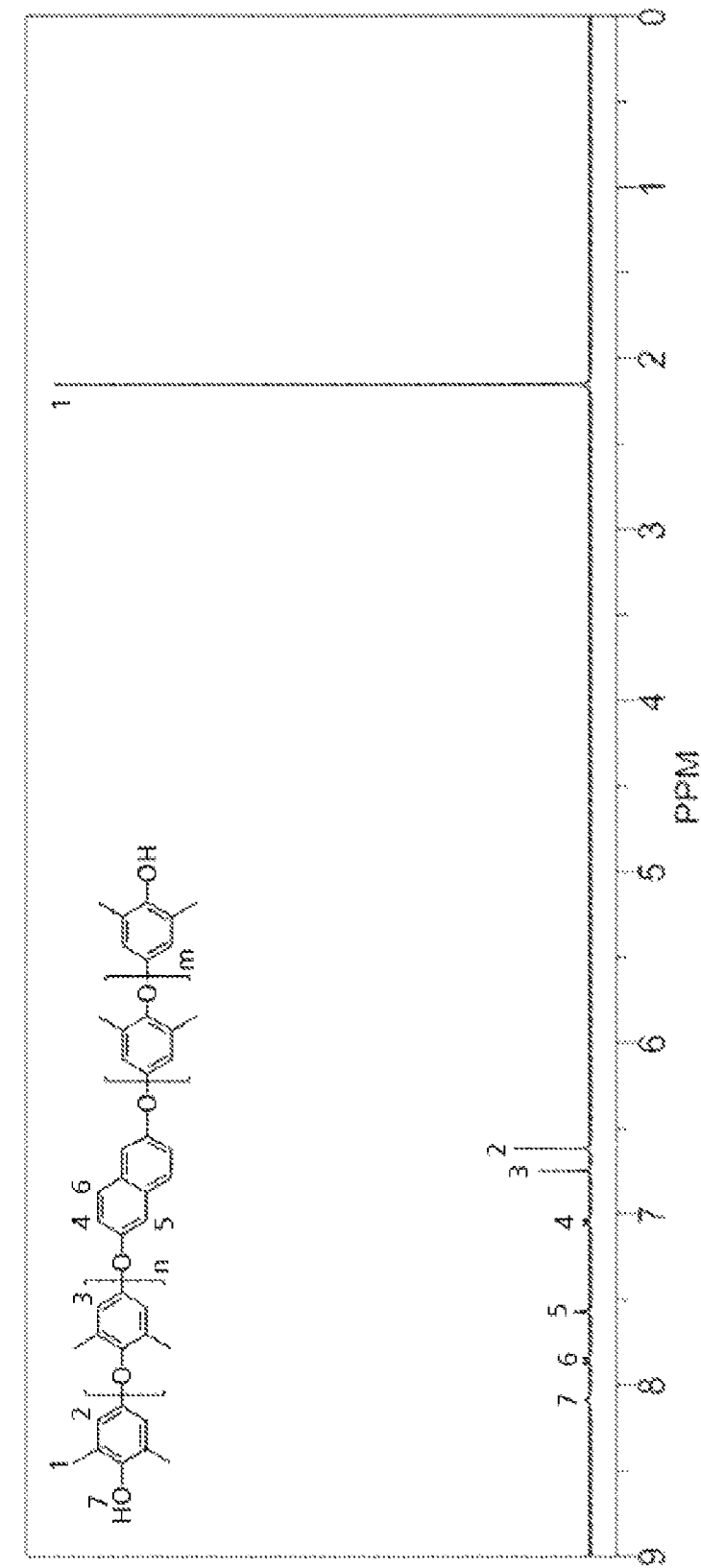
FIG. 5 is a $^1$H-NMR graph of the compound prepared in Example 3.

$^1$H-NMR of the compound is shown in FIG. 5.

(2) Preparation of Copolycarbonate

A copolycarbonate resin was prepared in the same manner as in Example 1, except that 26.3 g of 4,4'-(((naphthalene-2,6-diylbis(oxy))bis(2,6-dimethyl-4,1-phenylene))bis(oxy))bis(2,6-dimethylphenol) was used instead of 26.3 g of 4,4'-(((1,4-phenylenebis(oxy))bis(2,6-dimethyl-4,1-phenylene))bis(oxy))bis(2,6-dimethylphenol) in the above (2) Preparation of copolycarbonate of Example 1 (molar ratio of Chemical Formula 1: Chemical Formula 2=about 10:90).

Figure 6:
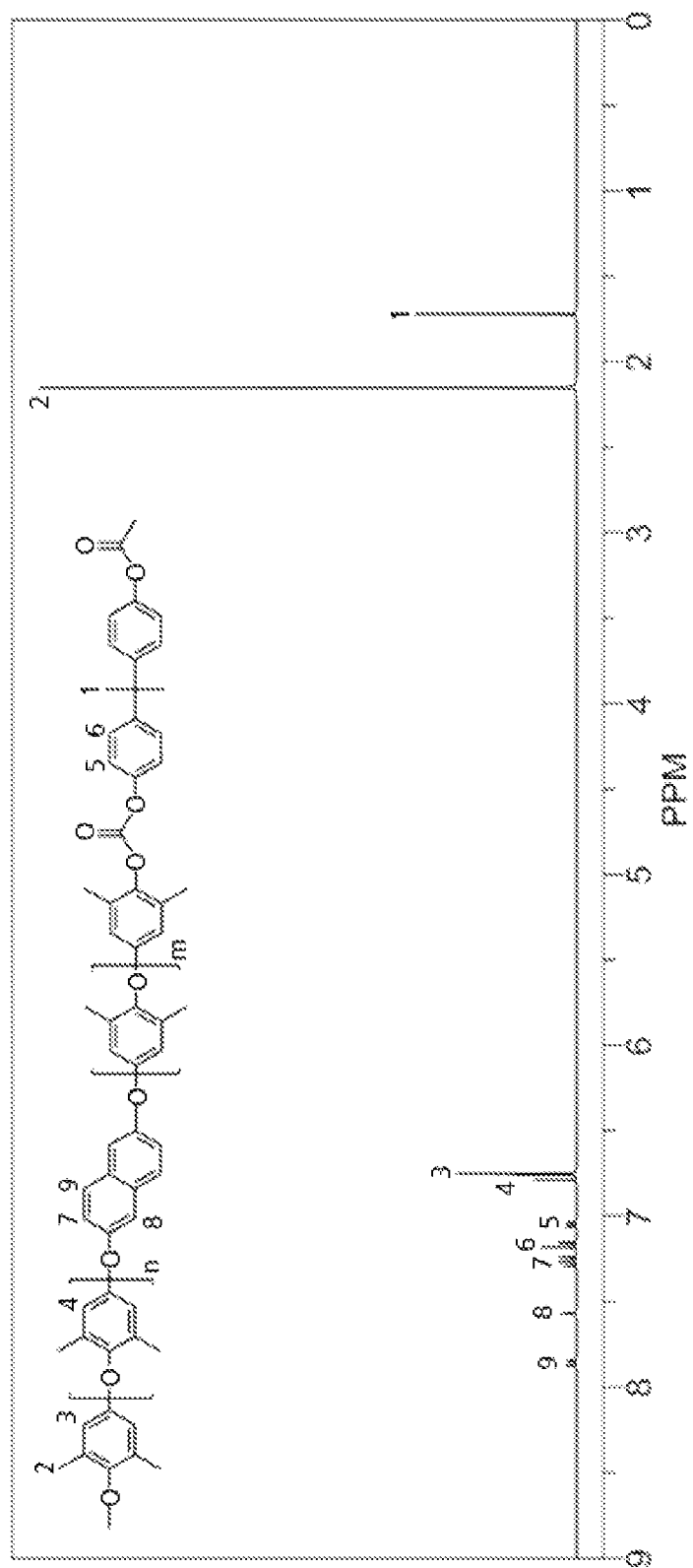
FIG. 6 is a $^1$H-NMR graph of the copolycarbonate prepared in Example 3.

$^1$H-NMR of the copolycarbonate thus prepared is shown in FIG. 6.

Example 4

(1) Preparation of monomer 4,4'-(((((hexahydrofuro[3,2-b]furan-3,6-diyl)bis(oxy))bis(2,6-dimethyl-4,1-phenylene))bis(oxy))bis(2,6-dimethylphenol)

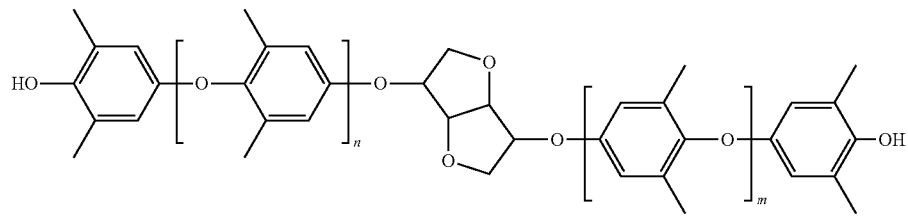

A compound with the above structure was prepared in the form of about 35.3 g of white powder in the same manner as in Example 1, except that 1.8 g of isosorbide (roquette, POLYSORB®) was used instead of 1.3 g of hydroquinone in the above (1) Preparation of monomer of Example 1 (Mw=2,000 g/mol, n,m=14~18).

Figure 7:
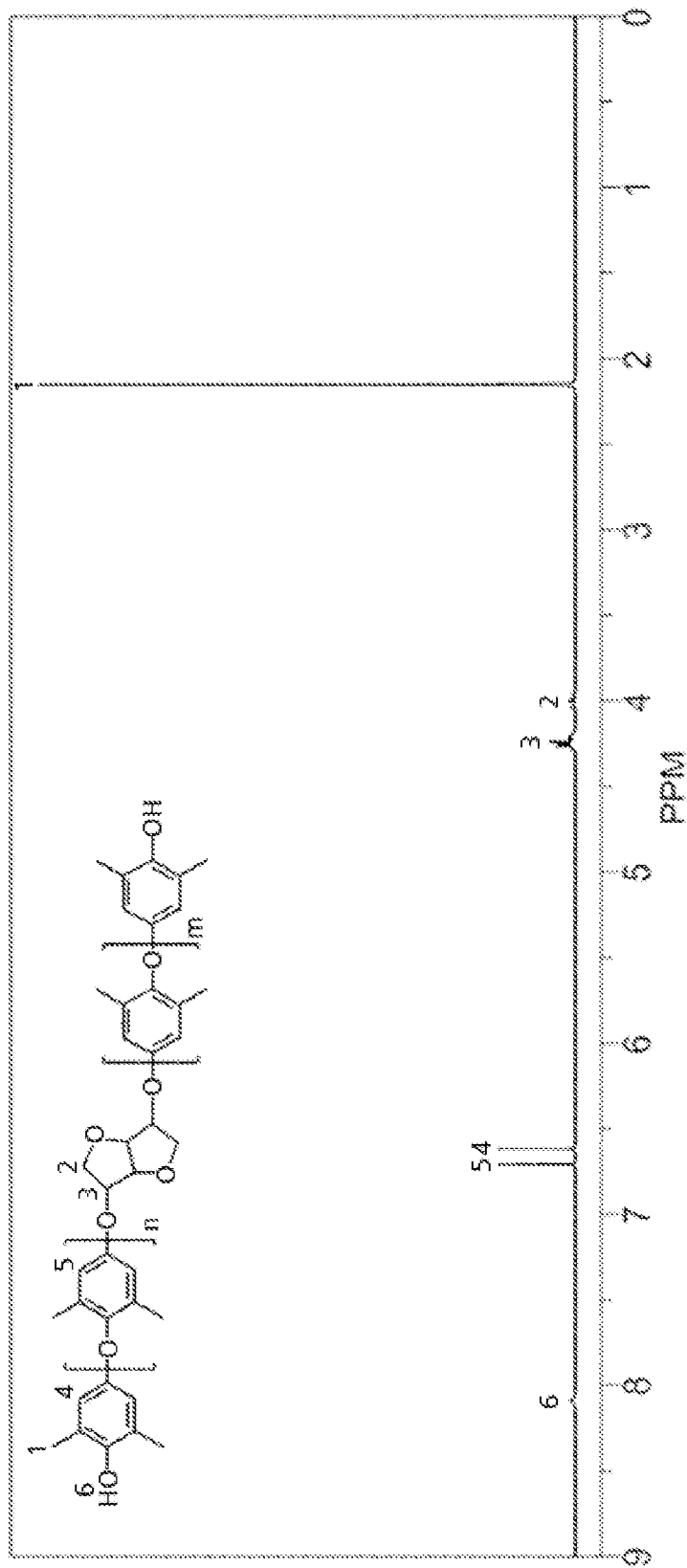
FIG. 7 is a $^1$H-NMR graph of the compound prepared in Example 4.

$^1$H-NMR of the compound is shown in FIG. 7.

(2) Preparation of Copolycarbonate

A copolycarbonate resin was prepared in the same manner as in Example 1, except that 26.3 g of 4,4'-(((((hexahydrofuro[3,2-b]furan-3,6-diyl)bis(oxy))bis(2,6-dimethyl-4,1-phenylene))bis(oxy))bis(2,6-dimethylphenol) was used instead of 26.3 g of 4,4'-(((1,4-phenylenebis(oxy))bis(2,6-dimethyl-4,1-phenylene))bis(oxy))bis(2,6-dimethylphenol) in the above (2) Preparation of copolycarbonate of Example 1 (molar ratio of Chemical Formula 1: Chemical Formula 2=about 10:90).

Figure 8:
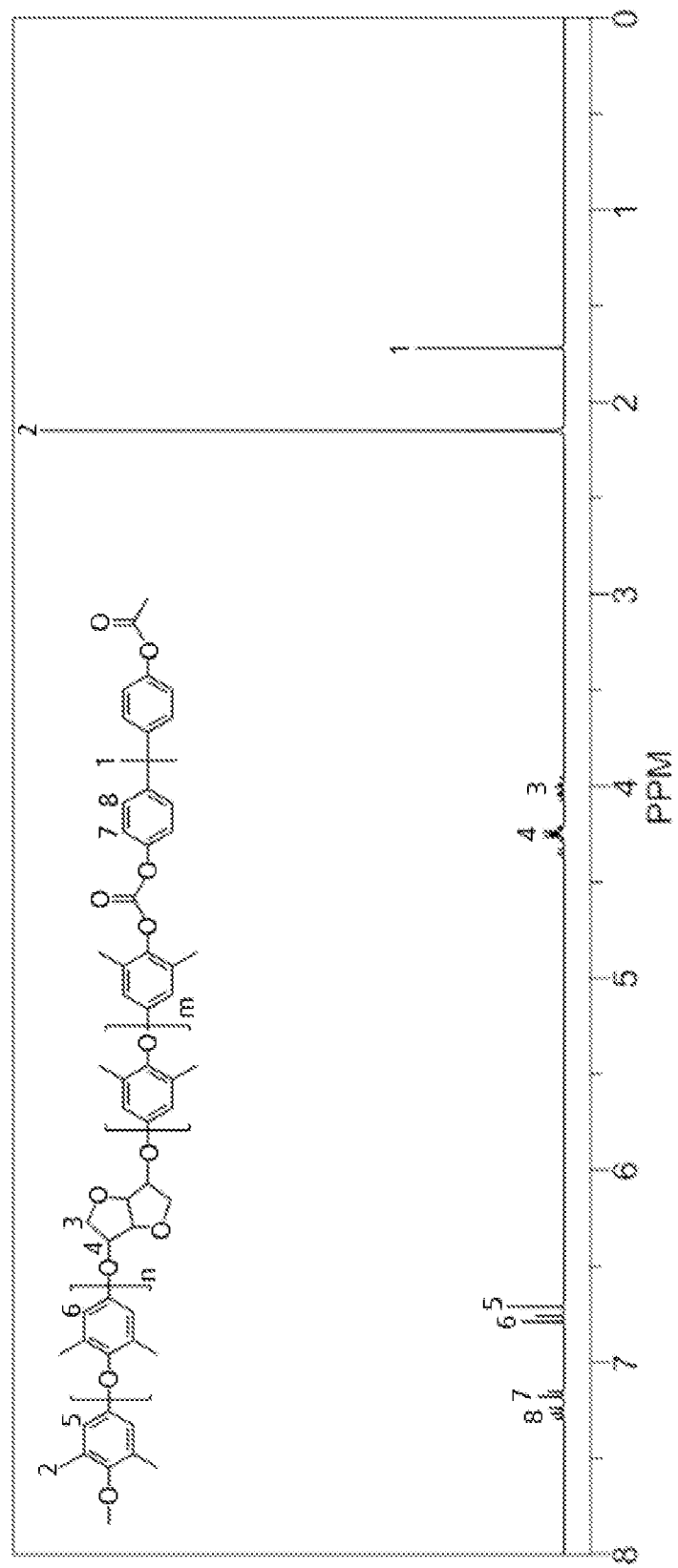
FIG. 8 is a $^1$H-NMR graph of the copolycarbonate prepared in Example 4.

$^1$H-NMR of the copolycarbonate thus prepared is shown in FIG. 8.

Comparative Example 1

90 wt % of commercialized polycarbonate (LUPOY PC P1300-10, manufactured by LG Co.) and 10 wt % of general PPO (polyphenylene oxide, Mw=2,000 g/mol) of the following Chemical Formula 5 were mixed and pelletized using a HAAKE Mini CTW extruder.

Chemical Formula 5

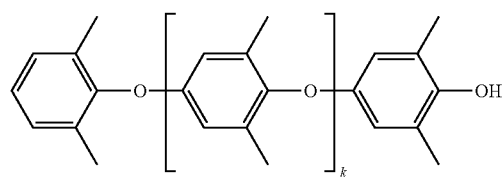

Comparative Example 2

A copolycarbonate resin was prepared in the same manner as in Example 1, except that 26.3 g of general PPO (polyphenylene oxide) of the following Chemical Formula 5 was used instead of 26.3 g of 4,4'-(((1,4-phenylenebis(oxy))bis(2,6-dimethyl-4,1-phenylene))bis(oxy))bis(2,6-dimethylphenol) in the above (2) Preparation of copolycarbonate of Example 1.

Chemical Formula 5

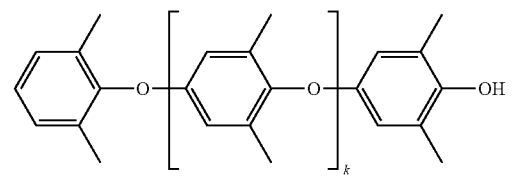

Comparative Example 3

(1) Preparation of monomer 4,4'-(((((propane-2,2-diylbis(4,1-phenylene))bis(oxy))bis(2,6-dimethyl-4,1-phenylene))bis(oxy))bis(2,6-dimethylphenol)

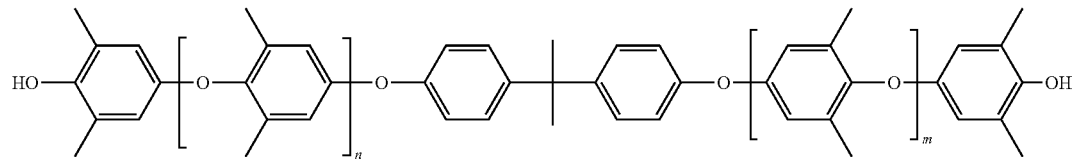

A compound with the above structure was prepared in the form of about 37.8 g of white powder in the same manner as in Example 1, except that 2.7 g of bisphenol A (BPA) was used instead of 1.3 g of hydroquinone in the above (1) Preparation of monomer of Example 1 (Mw=2,300 g/mol, n,m=14~18).

(2) Preparation of Copolycarbonate

A copolycarbonate resin was prepared in the same manner as in Example 1, except that 26.3 g of 4,4'-((((propane-2,2-diylbis(4,1-phenylene))bis(oxy))bis(2,6-dimethyl-4,1-phenylene))bis(oxy))bis(2,6-dimethylphenol) was used instead of 26.3 g of 4,4'-(((1,4-phenylenebis(oxy))bis(2,6-dimethyl-4,1-phenylene))bis(oxy))bis(2,6-dimethylphenol) in the above (2) Preparation of copolycarbonate of Example 1.

EXPERIMENTAL EXAMPLES

Evaluation of Physical Properties of Polycarbonate 0.050 part by weight of tris(2,4-di-tert-butylphenyl) phosphite, 0.010 part by weight of octadecyl-3-(3,5-di-tert-butyl-4-hydroxyphenyl) propionate, and 0.030 part by weight of pentaerythritol tetrastearate were added to 100 parts by weight of each polycarbonate resin prepared in Examples and Comparative Examples, and pelletized using HAAKE Mini CTW with a vent. Then, it was injection molded at a cylinder temperature of 300° C. and a mold temperature of 120° C. using a HAAKE Minijet injection molding machine to prepare a specimen.

The characteristics of injection-molded specimens or copolycarbonates were measured by means of the following method, and the results are shown in Table 1.

*Repeating unit: Measured by $^1$H-NMR using Varian 500 MHz.

*Weight average molecular weight (g/mol): Measured using Agilent 1200 series and calibrated with polystyrene standard (PS standard).

*Flowability (MI): Measured in accordance with ASTM D1238 (300° C., 1.2 kg condition).

*Izod impact strength (J/m): Measured at 23° C. in accordance with ASTM D256 (⅛ inch, Notched Izod).

*Glass transition temperature (Tg, ° C.): Measured using DSC (manufactured by TA Instrument).

*Pencil hardness: Measured using a pencil hardness tester (manufactured by Cometech) with a pencil of 2B, B, HB strength at a 45 degree angle with a load of 50 g in accordance with ASTM D3363.

TABLE 1

| | Mw (g/mol) | MI (g/10 min) | Izod impact strength (J/m) | Tg (° C.) | Pencil hardness |
|---|---|---|---|---|---|
| Example 1 | 30,800 | 10.1 | 330 | 155 | B |
| Example 2 | 31,300 | 9.4 | 280 | 153 | B |
| Example 3 | 31,000 | 9.9 | 350 | 161 | B |
| Example 4 | 30,500 | 10.6 | 250 | 156 | HB |
| Comparative Example 1 | 31,100 | 9.7 | 340 | 147 | 2B |
| Comparative Example 2 | 28,300 | 14.7 | 230 | 149 | 2B |
| Comparative Example 3 | 30,800 | 10.1 | 320 | 152 | 2B |

Referring to Table 1, it was confirmed that the polycarbonate including the repeating unit derived from the diol compound of Chemical Formula 1 of the present disclosure exhibited very high glass transition temperature of 153° C. or higher, and thus had significantly improved heat resistance compared to Comparative Example 1 in which general PPO was simply blended and Comparative Example 2 prepared using simple PPO that does not include a substituent R.

In addition, although Comparative Examples 1 to 3 had the pencil hardness of 2B, the polycarbonate of the present disclosure exhibited high hardness of B or HB.

Accordingly, it can be confirmed that the polycarbonate including the repeating unit derived from the diol compound of Chemical Formula 1 of the present disclosure could achieve improved heat resistance, impact resistance, and increased hardness at the same time compared to compounds obtained by blending or polymerizing general PPO with a polycarbonate.

What is claimed is:

1. A diol compound of Chemical Formula 1:

Chemical Formula 1

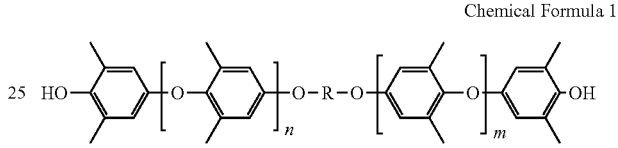

wherein in Chemical Formula 1:
R is a divalent group derived from benzene, unsubstituted biphenyl, terphenyl, or naphthalene; $C_{3-20}$ cycloalkylene unsubstituted or substituted with $C_{1-10}$ alkyl; or $C_{3-20}$ heterocycloalkylene unsubstituted or substituted with $C_{1-10}$ alkyl; and
n and m are each independently an integer from 1 to 1,000.

2. The diol compound of claim 1,
wherein R is a divalent group of one of the following formulae:

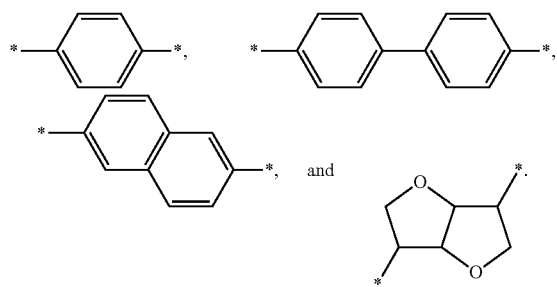

3. A polycarbonate, comprising a diol compound of the following Chemical Formula 1, a compound of the following Chemical Formula 2, and a repeating unit derived from a carbonate precursor:

Chemical Formula 1

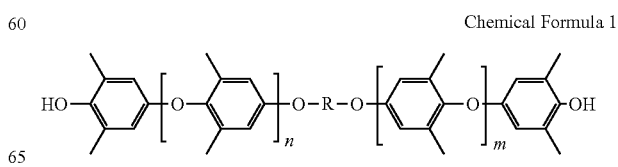

wherein in Chemical Formula 1:
R is a divalent group derived from benzene, unsubstituted biphenyl, terphenyl, or naphthalene; $C_{3-20}$ cycloalkylene unsubstituted or substituted with $C_{1-10}$ alkyl; or $C_{3-20}$ heterocycloalkylene unsubstituted or substituted with $C_{1-10}$ alkyl, and
n and m are each independently an integer from 1 to 1,000, Chemical Formula 2

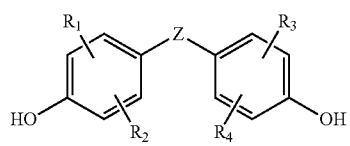

wherein in Chemical Formula 2:
$R_1$ to $R_4$ are each independently hydrogen, $C_{1-10}$ alkyl, $C_{1-10}$ alkoxy, or halogen; and
Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

4. The polycarbonate of claim 3,
wherein R is a divalent group of one of the following formulae:

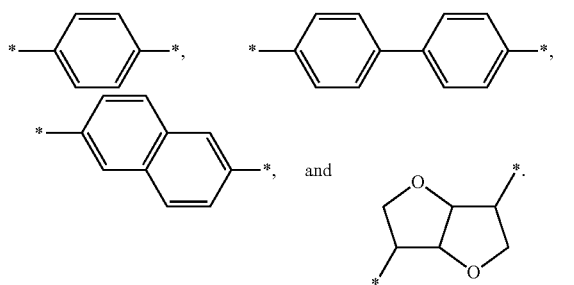

5. The polycarbonate of claim 3,
wherein $R_1$ to $R_4$ are each independently hydrogen, or $C_{1-4}$ alkyl.

6. The polycarbonate of claim 3,
wherein a molar ratio of a repeating unit derived from the compound of Chemical Formula 1 and a repeating unit derived from the compound of Chemical Formula 2 is 99:1 to 1:99.

7. The polycarbonate of claim 3,
wherein the polycarbonate has a weight average molecular weight (Mw) of 15,000 to 50,000 g/mol, measured by GPC using PS Standard.

8. The polycarbonate of claim 3,
comprising a repeating unit of the following Chemical Formula 3:

Chemical Formula 3

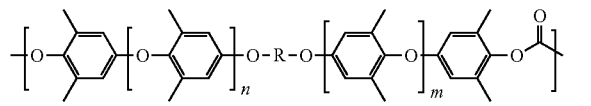

wherein in Chemical Formula 3:
R is a divalent group derived from benzene, unsubstituted biphenyl, terphenyl, or naphthalene; $C_{3-20}$ cycloalkylene unsubstituted or substituted with $C_{1-10}$ alkyl; or $C_{3-20}$ heterocycloalkylene unsubstituted or substituted with $C_{1-10}$ alkyl, and
n and m are each independently an integer from 1 to 1,000.

9. The polycarbonate of claim 3,
comprising a repeating unit of the following Chemical Formula 4:

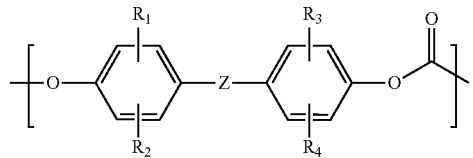

wherein in Chemical Formula 4:
$R_1$ to $R_4$ are each independently hydrogen, $C_{1-10}$ alkyl, $C_{1-10}$ alkoxy, or halogen; and
Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

10. The polycarbonate of claim 3,
wherein the polycarbonate has an Izod impact strength at room temperature of 100 to 1,000 J/m, measured at 23° C. in accordance with ASTM D256 (⅛ inch, Notched Izod).

11. The polycarbonate of claim 3,
wherein the polycarbonate has a glass transition temperature (Tg) of 153 to 190° C.

12. The polycarbonate of claim 3,
wherein the polycarbonate has pencil hardness of B or HB, measured at a 45 degree angle with a load of 50 g in accordance with ASTM D3363.

13. A method of preparing a polycarbonate, comprising a step of polymerizing a composition containing a compound of the following Chemical Formula 1, an aromatic diol compound of the following Chemical Formula 2 and a carbonate precursor:

Chemical Formula 1

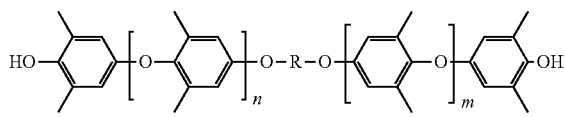

wherein in Chemical Formula 1:
R is a divalent group derived from benzene, unsubstituted biphenyl, terphenyl, or naphthalene; $C_{3-20}$ cycloalkylene unsubstituted or substituted with $C_{1-10}$ alkyl; or $C_{3-20}$ heterocycloalkylene unsubstituted or substituted with $C_{1-10}$ alkyl; and
n and m are each independently an integer from 1 to 1,000,

[Chemical Formula 2]

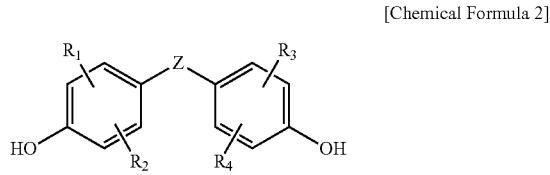

wherein in Chemical Formula 2:

$R_1$ to $R_4$ are each independently hydrogen, $C_{1-10}$ alkyl, $C_{1-10}$ alkoxy, or halogen; and Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

14. The method of claim 13, wherein R is a divalent group of one of the following formulae:

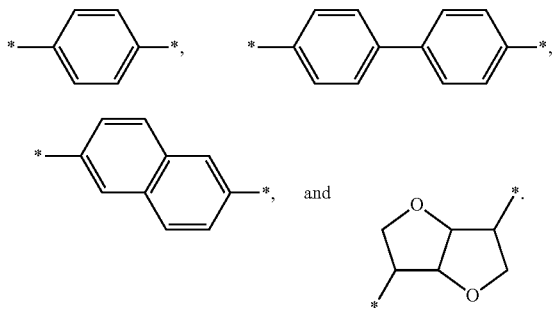

15. The method of claim 13, wherein the aromatic diol compound of Chemical Formula 2 is at least one compound selected from the group consisting of bis(4-hydroxyphenyl)methane, bis (4-hydroxyphenyl)ether, bis(4-hydroxyphenyl)sulfone, bis(4-hydroxyphenyl)sulfoxide, bis(4-hydroxyphenyl) sulfide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane (bisphenol Z), 2,2-bis (4-hydroxy-3,5-dibromophenyl)propane, 2,2-bis (4-hydroxy-3,5-dichlorophenyl)propane, 2,2-bis(4-hydroxy-3-bromophenyl)propane, 2,2-bis(4-hydroxy-3-chlorophenyl)propane, 2,2-bis (4-hydroxy-3-methylphenyl)propane, 2,2-bis(4-hydroxy-3,5-dimethylphenyl)propane, and 1,1-bis(4-hydroxyphenyl)-1-phenylethane.

16. The method of claim 13, wherein the polymerization is carried out by a melt polymerization method.

17. The method of claim 16, wherein a carbonic acid diester compound is used as a carbonate precursor during the melt polymerization.

18. A molded article, comprising the polycarbonate of claim 3.

* * * * *